United States Patent
Rappel et al.

(10) Patent No.: US 9,539,354 B2
(45) Date of Patent: Jan. 10, 2017

(54) FRAGRANCE DISCHARGE DEVICE

(71) Applicant: MAHLE International GmbH, Stuttgart (DE)

(72) Inventors: Thomas Rappel, Stuttgart (DE); Dieter Sartorius, Vaihingen/Enz (DE); Matthias Uhle, Leutenbach (DE)

(73) Assignee: MAHLE International GmbH, Stuttgart (DE)

( * ) Notice: Subject to any disclaimer, the term of this patent is extended or adjusted under 35 U.S.C. 154(b) by 0 days.

(21) Appl. No.: 14/550,361

(22) Filed: Nov. 21, 2014

(65) Prior Publication Data
US 2015/0144711 A1 May 28, 2015

(30) Foreign Application Priority Data
Nov. 22, 2013 (DE) .......................... 10 2013 223 955

(51) Int. Cl.
*A61L 9/12* (2006.01)
*B60H 3/00* (2006.01)

(52) U.S. Cl.
CPC .............. *A61L 9/12* (2013.01); *B60H 3/0014* (2013.01); *B60H 2003/0057* (2013.01)

(58) Field of Classification Search
CPC ...... A61L 9/04; A61L 9/12; B60H 2003/0057; B60H 3/0014; B60H 3/0007
USPC ........................................ 239/55, 57, 58, 59
See application file for complete search history.

(56) References Cited

U.S. PATENT DOCUMENTS

| | | | |
|---|---|---|---|
| 4,523,870 A * | 6/1985 | Spector ..................... | A61L 9/12 239/55 |
| 5,050,798 A * | 9/1991 | Sullivan .................... | A61L 9/01 221/66 |
| 5,368,822 A | 11/1994 | McNeil | |
| 2006/0049270 A1 * | 3/2006 | Wayne ....................... | A47F 5/02 239/57 |
| 2007/0194368 A1 | 8/2007 | Caserta et al. | |
| 2008/0093474 A1 | 4/2008 | Suissa et al. | |
| 2009/0188952 A1 | 7/2009 | Boyd | |

FOREIGN PATENT DOCUMENTS

DE 10 2005 025 755 A1 1/2006
DE 10 2012 009 676 A1 10/2012

* cited by examiner

*Primary Examiner* — Christopher Kim
(74) *Attorney, Agent, or Firm* — Muncy, Geissler, Olds & Lowe, P.C.

(57) ABSTRACT

A fragrance discharge device for discharging at least one fragrance, having a housing through which air can flow, having at least one fragrance cartridge arranged therein, wherein a drawer is provided so it is displaceable in the housing, for accommodating and holding at least one fragrance cartridge, wherein the drawer can be pulled at least partially out of the housing to replace the at least one fragrance cartridge, wherein the fragrance cartridge is connectable to the drawer via a magnetic force.

9 Claims, 3 Drawing Sheets

FRAGRANCE DISCHARGE DEVICE

This nonprovisional application claims priority to German Patent Application No. DE 10 2013 223 955.6, which was filed in Germany on Nov. 22, 2013, and which is herein incorporated by reference.

BACKGROUND OF THE INVENTION

Field of the Invention

The present invention relates to a fragrance discharge device, in particular for a motor vehicle.

Description of the Background Art

Fragrance discharge devices are known in the prior art for motor vehicles, for example, from DE 10 2012 009 676 A1. Fragrance discharge devices are becoming more and more widespread, because they have a very memorable influence on the well-being of vehicle occupants with the fragrance emitted thereby.

The fragrance discharge devices according to the prior art also sometimes enable the passengers of a vehicle to be able to design the fragrance experience in their own vehicle individually according to their desire and their mood. For this purpose, fragrance discharge devices having two fragrance cartridges are known, for example, in which the discharged fragrance is changeable accordingly by a change of the fragrance cartridge. It is possible via operating elements to switch back and forth very rapidly and easily, also during travel, between the two inserted fragrances.

The fragrance cartridges are arranged in this case in a type of drawer, which is extendable out of a housing. If the drawer is aligned horizontally, the fragrance cartridges can simply be laid therein. In contrast, if the drawer is aligned vertically, the fragrance cartridges are removed toward the side, wherein special measures are to be taken against the fragrance cartridges falling out.

For reasons of installation space, if two fragrance cartridges are used, they are very close to one another, so that the removal of the fragrance cartridges is made more difficult. The fragrance cartridges are only laid in the drawer in this case, so that the pivot angle of the fragrance cartridges must be limited to prevent them from falling out.

SUMMARY OF THE INVENTION

It is therefore an object of the present invention to provide an improved fragrance discharge device, which is also improved with regard to the accommodation of fragrance cartridges.

An exemplary embodiment of the invention relates to a fragrance discharge device for discharging at least one fragrance, having a housing, through which air can flow, having at least one fragrance cartridge arranged therein, wherein a drawer is provided so it is displaceable in the housing, for accommodating and holding at least one fragrance cartridge, wherein the drawer can be pulled at least partially out of the housing to replace the at least one fragrance cartridge, wherein the fragrance cartridge is connectable by means of magnetic force to the drawer. Secure fastening can thus be achieved with good detachability at the same time.

For this purpose, it is particularly advantageous if a magnetic element is provided on the cartridge and/or on the drawer. This magnetic element can be a magnet, which exerts a magnetic force. Magnets having rare earth elements are advantageous for this purpose in particular, because they achieve a high level of magnetization.

It is also advantageous if a metallic and/or magnetizable element is provided on the cartridge and/or on the drawer. This metallic and/or magnetizable element is then attracted by a magnet.

It is advantageous in this case if the drawer has an end wall, on which the magnetic element or elements and/or the metallic and/or magnetizable element or elements are provided. The fragrance cartridge can thus be fastened on this end wall.

It is also advantageous if the magnetic element or elements and/or the metallic and/or magnetizable element or elements is/are fixedly connected to the end wall or is/are arranged movably in relation thereto. The fixed connection is easy to achieve during the assembly, while the movable arrangement permits certain degrees of freedom during the removal of the fragrance cartridges.

It is particularly advantageous if the end wall is articulated and/or displaceably arranged in the drawer.

In an embodiment, the end wall can be articulated and/or displaceably arranged in the housing of the drawer.

Furthermore, The end wall can be guided in rails of the housing of the drawer. The displaceability during the removal or pushing in of the drawer may thus be controlled.

In an embodiment, the end wall can be connected via at least one lever arm to the housing of the drawer and is guided on both sides via rails.

Furthermore, one end wall can be provided in each case for each placeable cartridge. Improved individual removal or insertion of the fragrance cartridge can thus be achieved.

The invention enables, via the above-described embodiment features, fastening of the fragrance cartridges in the drawer to be easily possible, and for this to be substantially independent of the orientation of the drawer. The fragrance cartridge can therefore be substantially prevented from falling out unintentionally.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

The invention relates to a fragrance discharge device, in particular for a motor vehicle, for discharging at least one fragrance. Various illustrations for explaining the invention are shown in FIGS. 1 to 7.

The fragrance discharge device has a housing 1, through which air can flow, wherein at least one fragrance cartridge 2 can be arranged in the housing 1. Preferably, two or more fragrance cartridges can also be provided, which can be arranged in the housing. To select a fragrance for scenting the air flowing through, a fragrance cartridge can be selected, the fragrance of which flows out in the air.

At least one drawer 3, which is used for accommodating and holding at least one fragrance cartridge 2, is provided so it is displaceable in the housing 1.

To replace a fragrance cartridge 2, the at least one drawer 3 is designed so it can be pulled at least partially out of the housing 1. In this case, the drawer can be guided in the housing by means of rails or the like. The at least one fragrance cartridge 2 is connectable in this case by means of magnetic force to the drawer, to hold the fragrance cartridge in the drawer.

Figure 1:
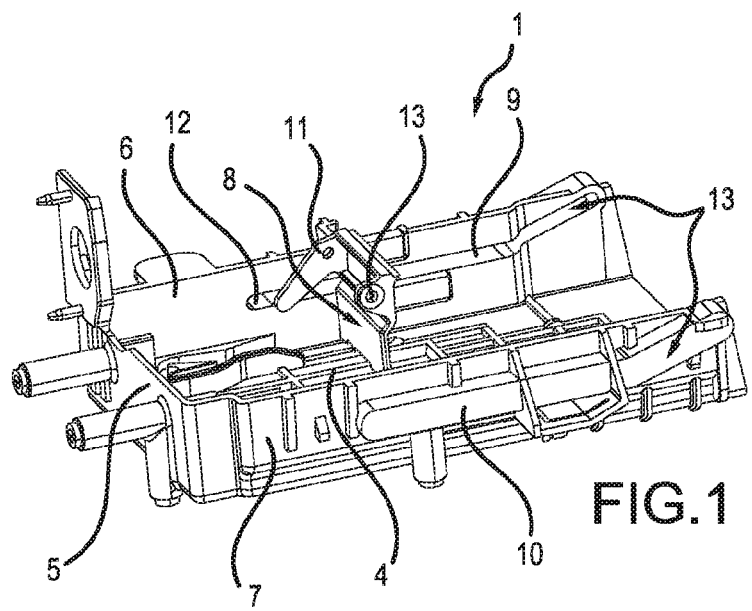
FIG. 1 shows a perspective view of a housing of a fragrance discharge device.

FIG. 1 shows a housing 1 for accommodating a drawer. The housing is implemented with a bottom 4 and three walls 5, 6, 7 arranged around it, wherein the walls 6, 7 accommodate the drawer between them as side walls. The wall 5 is used as a terminus wall and has pins for insertion of the housing 1 into the vehicle or other housing parts. A displaceable end wall 8, which is displaceably guided in grooves 9, 10 of the housing in the region of the walls 6, 7, is provided between the walls 6, 7. In this case, the end wall 8 is also mounted so it is tiltable. The end wall 8 has a lever arm 11 having a pin 12, which is guided in the grooves 9, 10. Since the grooves 9, 10 do not have a linear profile, but rather rise at the end region of the housing, this causes tilting of the end wall 8 as soon as the pin 12 reaches the rising part 13 of the grooves 9, 10 and is moved therein.

Figures 2, 3:
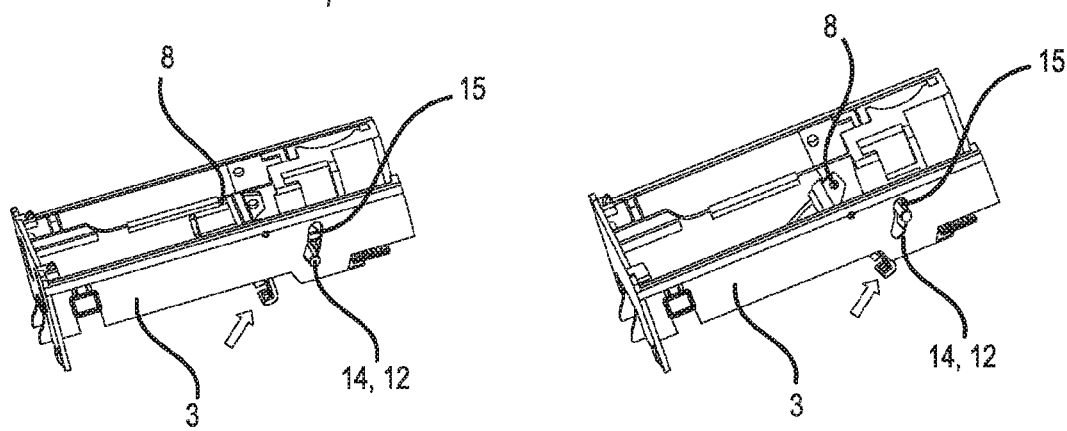
FIG. 2 shows a perspective view of a drawer for use in the housing according to FIG. 1.
FIG. 3 shows a perspective view of a drawer for use in the housing according to FIG. 1.
Figure 4:
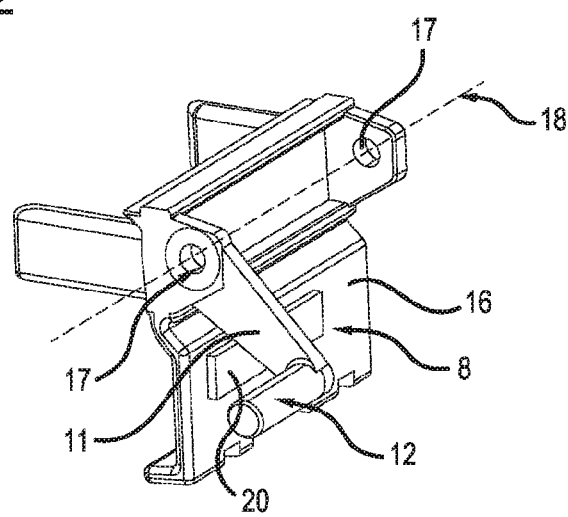
FIG. 4 shows an end wall of the drawer.

FIGS. 2 and 3 show the drawer 3, in which the end wall 8 is arranged pivotably mounted. In this case, the end wall 8 is guided by means of lateral bolts 14 as pins 12 in a groove and is pivotably mounted in the axis 18. FIG. 2 shows an operating position in which the end wall of FIG. 4 is aligned essentially vertically, as shown in FIG. 4. In FIG. 3, the end wall of FIG. 4 is pivoted forward into a removal position.

Figure 8:
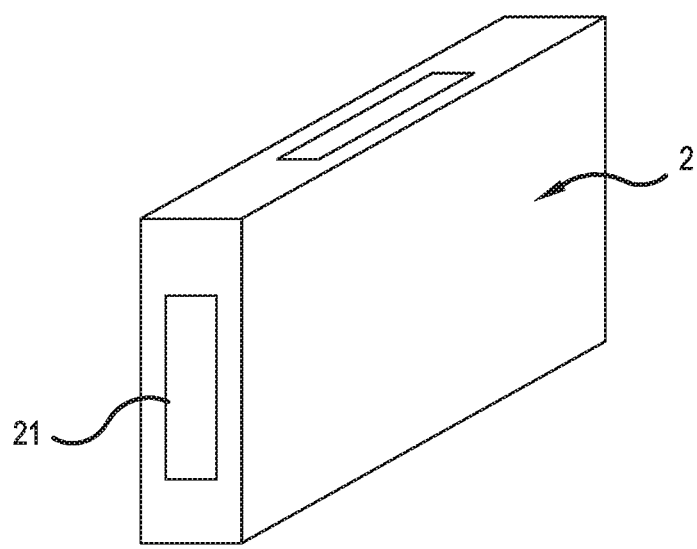
FIG. 8 shows a perspective view of a fragrance cartridge.

To fasten the fragrance cartridge 2 on the end wall 8, a magnetic element 20 is provided on the fragrance cartridge 2 and/or on the drawer 3, for example, in particular on the end wall 8 (as shown in FIG. 4). This element 20 is, for example, a permanent magnet, for example, having a magnet or made of a magnet, in particular having rare earth elements. For the fastening, it is advantageous if a metallic and/or magnetizable element 21 is provided on the fragrance cartridge 2 (as shown in FIG. 8) and/or on the drawer 3, in particular on the end wall 8. This element 21 is attracted and fastened by the magnetic element 20, such as magnets.

In a preferred exemplary embodiment, the drawer 3 has an end wall 8, on which the magnetic element or elements and/or the metallic and/or magnetizable element or elements are provided. FIG. 4 shows such an end wall 8 once again enlarged in detail. The end wall 8 has a wall surface 16, on which the fragrance cartridge can be applied and fastened by means of magnetic elements. Furthermore, the end wall 8 is articulated at the openings 17 along the axis 18 by means of bolts. The lever arm 11 with the pin 12 is provided for controlling a displacement.

In this case, the magnetic element or the magnetic elements and/or the metallic and/or magnetizable element or elements can be fixedly connected to the end wall 8 or arranged movably in relation thereto. In this case, it is advantageous if the magnetic element or the metallic element or the magnetizable element is connected to the wall surface 16, in particular glued thereon, for example. The metallic or magnetizable elements are preferably small metal plates, which can be provided on the fragrance cartridges.

Particularly wide pivoting out of the fragrance cartridges upon opening of the drawer for easy grasping of the fragrance cartridges can be achieved by the control of the inclination of the end wall by means of the lever arm 11 with the groove 9, 10.

To assist the removal of a fragrance cartridge, the other, in particular adjacent fragrance cartridge can be pressed in again without great application of force, wherein it can again pivot out independently when it is released.

Upon closing of the drawer, the fragrance cartridges then pivot automatically and in particular without touching the housing back into the drawer again. The wide pivoting out is implemented via the rotatable end wall 8 of the drawer 3. The end wall 8 is connected via lever arms 11 to the drawer housing and is guided on both sides via rails 9, 10. Upon opening of the drawer, the end wall 8 of the drawer 3 is rotated enough that the fragrance cartridges 2 pivot out of the drawer 3. Upon closing of the drawer 3, the end wall 8 is rotated back via the forced guide, and the fragrance cartridges 2 pivot back into the drawer 3.

The springing back of the fragrance cartridge can be implemented solely via the magnetic force. For this purpose, the magnets are also attached at a position which again causes the fragrance cartridge to press against the end wall in a formfitting manner due to its lever action.

Figure 5:
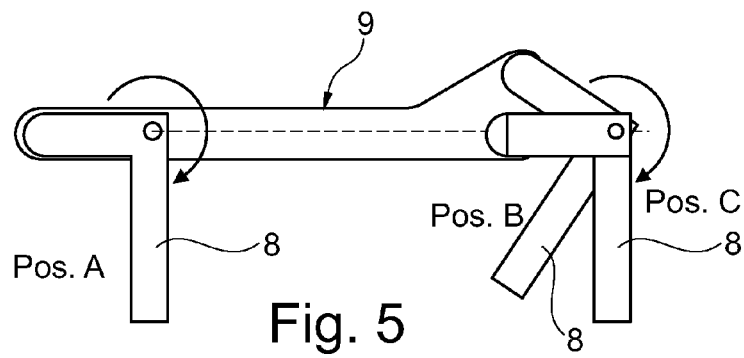
FIG. 5 shows a schematic illustration of the arrangement of the end wall with its possible pivot positions.

FIG. 5 shows an example of this. The end wall 8 is in position A in the position of the closed drawer. In position B, the end wall is in the position of the open drawer. In position C, the position is shown with open drawer but cartridge pressed down.

To implement greater pivot angles, the end wall is advantageously also spring mounted and the guide rails are adapted accordingly. Additional spring elements, for example, leg springs, act on the end wall in such a manner that it has the drive to pivot the fragrance cartridges out of the drawer. As soon as the drawer is opened, the lever of the end wall moves into the expanded region of the guide rail and the spring can rotate the end wall in accordance with the expansion. By pressing on a fragrance cartridge, it can pivot in against the spring force and the other cartridge can be easily removed. In this case, the magnetic and spring forces are adapted so that the cartridge does not fall out and the spring force can also be overcome. Easy detachment from the end wall in the region of the magnet is compensated for by the recovery action of the magnet.

Figure 6:
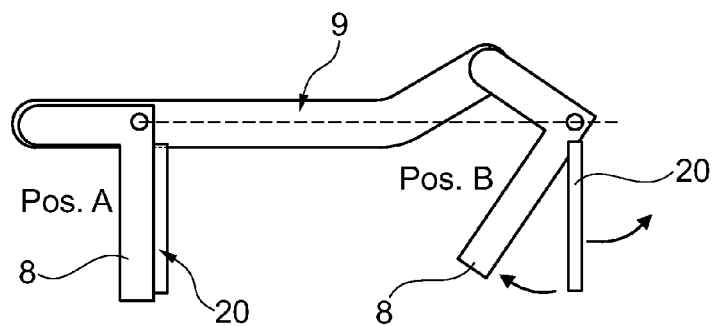
FIG. 6 shows a schematic illustration of the arrangement of the end wall with its possible pivot positions.
Figure 7:
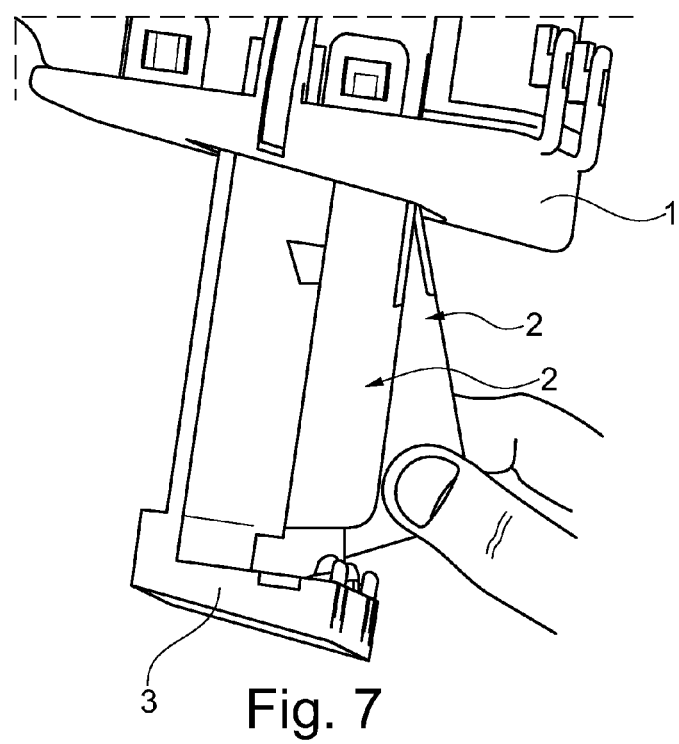
FIG. 7 shows a perspective partial view of a housing of a fragrance discharge device having a partially pulled-out drawer during the removal of a fragrance cartridge.

FIG. 6 shows an exemplary embodiment in which the magnetic elements 20 are displaceably connected to the end wall 8. The end wall 8 having the magnetic element 20 is in position A in the position of the open drawer. In position B, the end wall is in the position of the open drawer, wherein the magnetic element lifts off from the end wall 8 as it is pressed away. Because of the spring force and without pressing away, the magnetic element 20 would press against the end wall 8.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A fragrance discharge device for discharging at least one fragrance, the device comprising:
    a housing through which air flows;
    at least one fragrance cartridge arranged in the housing;
    a drawer displaceably arranged in the housing to accommodate and hold the at least one fragrance cartridge, the drawer being adapted to be at least partially pulled out of the housing to replace the at least one fragrance cartridge,
    wherein the fragrance cartridge is connectable via a magnetic force to the drawer,
    wherein the drawer includes an end wall provided therein that is mechanically coupled to the drawer in a pivotable manner, the end wall being pivotable with respect to the drawer and the housing,
    wherein the end wall is positioned so as to abut a side wall of the at least one fragrance cartridge,
    wherein the end wall is connected via at least one lever arm to the housing and the at least one lever arm is guided on a respective rail of the housing, and
    wherein at least one magnetic element, at least one metallic element or at least one magnetizable element is fixedly connected to the end wall.

2. The fragrance discharge device according to claim 1, wherein two of the at least one lever arm and two of the rail are provided, wherein the end wall is guided in the two rails of the housing by the two lever arms.

3. The fragrance discharge device according to claim 1, wherein the end wall pivots between a first position when the drawer is closed and a second position, having a different angle from the first position, when the drawer is partially pulled out of the housing.

4. A fragrance discharge device for discharging at least one fragrance, the device comprising:
    a housing through which air flows;
    at least one fragrance cartridge arranged in the housing;
    a drawer displaceably arranged in the housing to accommodate and hold the at least one fragrance cartridge, the drawer being adapted to be at least partially pulled out of the housing to replace the at least one fragrance cartridge,
    wherein the fragrance cartridge is connectable via a magnetic force to the drawer,
    wherein the drawer includes an end wall provided therein that is mechanically coupled to the drawer in a pivotable manner, the end wall being pivotable with respect to the drawer and the housing,
    wherein the end wall is positioned so as to abut a side wall of the at least one fragrance cartridge,
    wherein the end wall is connected via at least one lever arm to the housing and the at least one lever arm is guided on a respective rail of the housing,
    wherein at least one magnetic element is provided on the fragrance cartridge or on the drawer,
    wherein at least one metallic element or at least one magnetizable element is provided on the the fragrance cartridge or the drawer to which the at least one magnetic element is not provided, such that one of the fragrance cartridge or the drawer has the at least one magnetic element provided thereon and the other of the fragrance cartridge or the drawer has the at least one metallic element or the at least one magnetizable element provided thereon, and
    wherein one of the at least one magnetic element, the at least one metallic element or the at least one magnetizable element is provided on the end wall.

5. A fragrance discharge device for discharging at least one fragrance, the device comprising:
    a housing through which air flows;
    at least one fragrance cartridge arranged in the housing;
    a drawer displaceably arranged in the housing to accommodate and hold the at least one fragrance cartridge, the drawer being adapted to be at least partially pulled out of the housing to replace the at least one fragrance cartridge,
    wherein the fragrance cartridge is connectable via a magnetic force to the drawer,
    wherein the drawer includes an end wall provided therein that is mechanically coupled to the drawer in a pivotable manner, the end wall being pivotable with respect to the drawer and the housing,
    wherein the end wall is positioned so as to abut a side wall of the at least one fragrance cartridge,
    wherein the end wall is connected via at least one lever arm to the housing and the at least one lever arm is guided on a respective rail of the housing, and
    wherein at least one magnetic element is pivotally attached to the end wall.

6. A fragrance discharge device for discharging at least one fragrance, the device comprising:
    a housing through which air flows;
    at least one fragrance cartridge arranged in the housing;
    a drawer displaceably arranged in the housing to accommodate and hold the at least one fragrance cartridge, the drawer being adapted to be at least partially pulled out of the housing to replace the at least one fragrance cartridge,
    wherein the fragrance cartridge is connectable via a magnetic force to the drawer,
    wherein the drawer includes an end wall provided therein that is mechanically coupled to the drawer in a pivotable manner, the end wall being pivotable with respect to the drawer and the housing,
    wherein the end wall is positioned so as to abut a side wall of the at least one fragrance cartridge, and
    wherein the end wall includes a lever extending therefrom and a pin extending perpendicularly from the lever.

7. The fragrance discharge device according to claim 6, wherein the pin extends through an elongated slot of the drawer, such that a portion of the pin extends to an exterior of the drawer.

8. The fragrance discharge device according to claim 7, wherein the portion of the pin that extends to the exterior of the drawer engages with a groove rail provided on an interior surface of the housing.

9. The fragrance discharge device according to claim 8, according to claim 8, wherein the elongated slot is oriented substantially perpendicular to the groove rail.

* * * * *